United States Patent [19]

Brown, Jr.

[11] Patent Number: 4,942,128
[45] Date of Patent: Jul. 17, 1990

[54] MICROBIAL CELLULOSE MODIFIED DURING SYNTHESIS

[75] Inventor: R. Malcolm Brown, Jr., Austin, Tex.

[73] Assignee: Board of Regents, the University of Texas System, Austin, Tex.

[21] Appl. No.: 22,904

[22] Filed: Mar. 6, 1987

[51] Int. Cl.$^5$ .................. C12P 19/04; C12R 1/02; B32B 7/00; C08B 11/193

[52] U.S. Cl. .................. 435/101; 435/823; 435/165; 435/252.1; 435/277; 428/264; 536/88; 536/91; 536/96; 536/98

[58] Field of Search ............ 435/101, 823, 165, 252.1, 435/277; 536/88, 91, 96, 98; 428/264

[56] References Cited

U.S. PATENT DOCUMENTS 4,378,431 3/1983 Brown, Jr. .

FOREIGN PATENT DOCUMENTS 580595 12/1946 United Kingdom .
1570487 7/1980 United Kingdom .

OTHER PUBLICATIONS

Shimwell, 1956, *J. Inst. Brew.*, 62:339–343.
Bureau, 1987, *Proc. Nat. Acad. Sci. USA*, 84:6985–6989.
Sarko, 1978, TAPPI, 61:59–61.
C. H. Haigler et al., Journal of Cellular Biology, vol. 94, pp. 64–69.
Chemical Abstracts, vol. 91, Aug. 27, 1979, p. 474, Abstract No. 73152q, Columbus, OH, USA and JP-A-79 37 889 (AJINOMOTO CO., INC.) 20-0-3-1979, Abstract.
E. Correns et al.: "Zur Bildung und zum Ubermolekularen Aufbau von Bakteriencellulose", Cellular Chem. and Tech., vol. 9, 1975, pp. 449–469.
International Search Report, Mar. 16, 1989.
Brown et al., J. App. Polymer Sci., Applied Polymer Symposium 37:33–78 (1983).
Bergey's Manual of Systematic Biology, 1:268–276 (1984).
Hestrin et al., Biochem. J., 5-8:345–352.
Haigler et al., J. Cell Biol., 94:64–69 (1982).
Haigler et al., Cellulose and Other Natural Polymer Systems, Brown, ed., pp. 273–297 (1982).
Brown, The Ekman Days, 3:1–15 (1981).
Ben-Hayim et al., J. Cell Biol., 25:191–207 (1965).
Lin et al., Science, 230:822–825 (1985).
Brown et al., Science, 218:1141–1142 (1982).
White and Brown, Proc. Natl. Acad. Sci. USA, 78:1047–1051 (1981).
Haigler et al., Science, 210:903–906 (1980) and Haigler and Brown, J. Cell Biol., 83:70 Abstract No. CS268.
Brown et al., Proc. Natl. Acad. Sci. USA, 73:4565–4569 (1976).
Barman, Enzyme Handbook, Springer-Verlag, New York, p. 565 (1969).
Search Report of the Scientific and Patent Literature.

*Primary Examiner*—Ronald W. Griffin
*Assistant Examiner*—Pamela S. Webber
*Attorney, Agent, or Firm*—Arnold, White & Durkee

[57] ABSTRACT

The present invention involves a method of producing cellulose. This method comprises inoculating a quantity of nutrient medium comprising a polysaccharide derivative such as carboxymethylcellulose (CMC) with a cellulose-producing microorganism. The inoculated medium is then aerobically incubated to facilitate the production of cellulose. The step of substantially drying the cellulose may be added for certain products. Substantially dried cellulose resulting from this procedure is highly absorbent, tending to retain its absorbent properties during repeated wetting and drying, and is usable where such absorbency is desired.

A subject of the present invention is a composition of matter consisting essentially of such cellulose in a native or substantially dried form. Microbial cellulose produced in the presence of carboxymethyl cellulose may be substantially dried by many means known to those skilled in the art. This drying may be, for example, by washing with a non-aqueous hydrophilic solvent or by air-drying. Preferred non-aqueous solvents include alkyl alcohols or ketones having less than about six carbon atoms. When such non-aqueous solvents are used to dry the CMC-produced cellulose, the dried cellulose may have a resilient structure and possibly an elastic nature.

49 Claims, 3 Drawing Sheets

MICROBIAL CELLULOSE MODIFIED DURING SYNTHESIS

BACKGROUND OF THE INVENTION

The present invention relates to the modification of microbial cellulose during its synthesis by cellulose-producing microorganisms. This modification results from the presence of a substance which alters the formation of native cellulose structure. The prototypical structure-modifying substance is carboxymethylcellulose.

Cellulose may be produced by microorganisms of the Acetobacterium, Rhizobium, Alcaligenes, Agrobacterium, and Pseudomonas type (see, for example Brown, Jr. et al. J. Applied Polymer Science: Polymer Symposium (1983) V.37 pp 33–78). The growth of cellulose-producing microorganisms with production of cellulose may occur when said microorganisms are aerobically cultivated in an appropriate nutrient medium.

Appropriate nutrient media of the present invention generally include standard nutrient medium such as GYC which contains (g/liter of distilled water): yeast extract, 10.0; D-glucose, 50.0; $CaCO_3$, 30.0 and agar, 25.0. Various alternatives such as replacements for glucose or yeast extract, and omissions of agar or $CaCO_3$ are usable and well-known to those skilled in the art (Bergey's Manual of SYSTEMATIC BIOLOGY Vol. 1 pp 268–276, Krieg, ed. Williams and Wilkins, Baltimore/London (1984). The preferred nutrient medium used directly or with modifications described herein was that first described by Schramm and Hestrin (Hestrin et al. Biochem. J. Vol. 58 pp 345–352 (1954). The standard Schramm Hestrin (SH) medium contained (g/L): D-glucose, 20; peptone, 5; yeast extract, 5; dibasic sodium phosphate, 2.7, and citric acid monohydrate, 1.15 (pH adjusted to between about 3.5 and 5.5 with HCl). When Schramm Hestrin without glucose (SH-gluc) is designated, this indicates the above SH composition, but without the 10 g glucose/liter addition.

The cellulose produced by *Acetobacter xylinum* (formerly known as *Acetobacter aceti* subsp. xylinum and reclassified by the 1984 Bergy's Manual cited above as a subspecies of *Acetobacter pasteurianus* and *Acetobacter hansenii*) has been widely studied. In the present application the primarily studied cellulose-producing microorganism is termed "*Acetobacter xylinum*". It is understood that these several names may be used to indicate the same organism.

Fibrillar alterations of microbially-produced cellulose by agents such as CMC have been previously shown to occur, for example, by ultrastructural studies using techniques such as electron microscopy (Haigler et al., *J. Cell Biology*, Vol. 94 pp 64–69 (1982) and Ben-Hayim et al. *J. Cell Biology*, Vol. 25 pp 191–207 (1965)). However, nowhere before the present invention has any substance been found or suggested to facilitate the microbial production of a cellulose with greatly improved and/or unique macroscopic properties such as resiliency, elasticity, tensile strength, degree of water absorptivity or retention of absorbtive capacity after repeated wettings.

Cellulose assembled by a static aerobic culture of *Acetobacter xylinum* may be contained in a hydrophilic membrane known as a pellicle. This cellulose is quite strong when wet, but brittle when dried. One of the major obstacles in using the natural absorbency of this native bacterial cellulose has been its inability to effectively retain absorbancy through cycles of wetting and drying. In an effort to improve the physical properties of the cellulose, the present invention concerns including a cellulose derivative such as carboxymethylcellulose in the culture medium during microbial synthesis of cellulose. This inclusion altered the produced cellulose to result in a product which retained most of its native absorbancy through cycles of wetting and drying. One object of this invention is to significantly alter the physical properties of microbial cellulose product by cellulose derivatives or related substances in order to expand the material uses of this product. It is envisioned that there will be, for example, tremendous advantages in the uses of this product in the absorbent technology industries.

SUMMARY OF THE INVENTION

The present invention involves a method of producing a modified cellulose. This method comprises inoculating a quantity of nutrient medium containing between about 0.1% and about 5% cellulose derivative (more preferably between about 1% and about 4%) with a cellulose-producing microorganism. The inoculated medium is then aerobically incubated to facilitate the production of modified cellulose. The step of substantially drying the modified cellulose may be added to result in certain cellulosic products. The substantially dried cellulose resulting from this procedure is highly absorbent, tending to retain its absorbent properties during repeated wetting and drying cycles and is usable where such absorbency is desired. The cellulosic gel produced in the presence of CMC may itself be usable as an optically clear soft material.

One object of the present invention is to produce a composition of matter consisting essentially of modified cellulose in a native or substantially dried form. Modified cellulose produced in the presence of cellulose derivative may be substantially dried by many means known to those skilled in the art. This drying may be, for example, by washing with a non-aqueous hydrophilic solvent or by air-drying. Preferred non-aqueous solvents include alkyl alcohols or ketones having less than about six carbon atoms. When such non-aqueous solvents are used to dry the CMC-produced cellulose, the dried modified cellulose may have a resilient structure and possibly an elastic nature.

The preferred cellulose-producing microorganisms of the present invention are Acetobacter although other cellulose-producing microorganisms may be used.

In the practice of the present invention a preferred cellulose derivative is carboxymethylcellulose and is preferably present in the nutrient medium at a concentration between about 0.1 wt/vol % and about 5 wt/vol %. The carboxymethylcellulose usable in the practice of the present invention has a preferred degree of substitution of between about 0.4 and about 1.2 carboxymethyl groups per monosaccharide unit.

BRIEF DESCRIPTION OF THE PREFERRED EMBODIMENT

Microbial cellulose may be biosynthesized in the presence of a substance which acts to decrease the order of cellulose fibrillar structure. When such biosynthesis occurs, the product cellulose possesses new and useful properties. These new and useful properties may include, depending upon the particular processing steps employed: optical clarity; increased absorptive capacity; improved ability to retain absorptive capacity through cycles of wetting and drying; tensile strength; resilience, and elasticity.

The culture conditions of the present invention are aerobic in the classical sense. Aerobic culture involves the exposure of an inoculated nutrient medium to amounts of an oxygen-containing gas such as air sufficient to facilitate growth or metabolism. Unless otherwise indicated, *Acetobacter xylinum* ATCC no. 23769 or ATCC no. 53582 (strain NQ5) from the American Type Culture Collection, Rockville, Md. were used in the present studies.

Although carboxymethylcellulose is a preferred substance for production of such product cellulose, other substances, particularly other cellulose derivatives may be used to analogously alter the cellulose produced by cellulose-producing microorganisms. For example, other polysaccharide derivatives may be substituted for CMC in the processes and compositions described herein. These polysaccharide derivative substitutes for CMC include polysaccharides such as cellulose, starch or dextran having substituents groups such as alkyl, alkylcarboxy, alkylhydroxy, sulfate, sulfonic acid, or alkylphosphate. These derivatives are most preferably hydrophilic although cellulose itself is so hydrophilic that minor amounts of hydrophobic substituents such as methyl may be used.

Among the steps most commonly used to process microbial cellulose produced in the presence of substances altering fibrillar formation is one or more drying steps. Microbial cellulose is generally produced in a static aerobic culture as a pellicle which is a term referring to a gelatinous formation. Modes of culture which may not result in pellicle formation involve cultures under agitation or static cultures with cellulose being continuously withdrawn. A drying step maybe applied to the gelatinous microbial cellulose produced in the presence of a cellulose-altering substance. The drying step may be as simple as air-drying or may involve lyophilization or the extraction of water from the altered microbial cellulose by treatment with solvent. When solvent treatment is used, the solvent is preferably a hydrophilic solvent miscible with water. The drying step may be used in conjunction with one or more washing steps to remove any undesired materials from the cellulose.

The following examples are presented to describe preferred embodiments and utilities of the present invention and are not meant to limit this invention unless otherwise stated in the claims appended hereto.

EXAMPLE 1

Production of an Altered, Non-integrated Cellulose Gel using CMC

*Acetobacter xylinum* was grown for three days in Schramm and Hestrin medium lacking exogenous glucose, supplemented with CMC (source: Hercules Type 7MF, lot #45816; molecular weight 250,000; degree of substitution 0.7). The two concentrations of CMC used were 2% and 4% (W/V). About 100ml of media were placed in each Roux bottle for static aerobic culture.

At the end of the third day, a completely clear cellulosic gel had been synthesized throughout the entire liquid at both 2 and 4% concentrations of CMC. The pellicle was not an integral structure and fell apart during an attempt to remove the pellicle from the Roux bottle. The viscous pellicle of cellulose was examined with a polarizing microscope. When nutrient medium was wicked from the cover slip off to one side, a remarkable flow birefringence was observed. When examining the material with darkfield microscopy, it was possible to see individual ribbons of cellulose. These ribbons were not permanently interconnected, but easily slid past each other. Thus, the long cellulose ribbons behaved as a nematic liquid crystal.

One piece of cellulose formed in 2% CMC was air dried. When rehydrated with distilled water, this cellulose was very effective in its rehydration. For example, a dry piece weighting only 0.0134 g absorbed distilled water and constituted a total weight of 1.479 g. This particular piece was very gelatinous and fragile; however, when pulled across the surface of a piece of parafilm, the entire hydrated droplet could easily be moved.

EXAMPLE 2

Production of Optically Clear Cellulose Gel Using CMC

Conditions were similar to those described in Example 1, except that 1% CMC was added to SH medium (minus glucose) and cultured in Roux bottles for four days. The pellicle in the Roux bottle was very clear optically and gelatinous, and cellulose was formed throughout the bottom and surface of the liquid. The pellicle of cellulose grown in 1% CMC had physical integrity and could be removed from the Roux bottle although it was much more delicate than a cellulose pellicle formed in SH medium lacking CMC. Upon removal, the interior of the pellicle contained liquid medium. Thus, the pellicle was a three-dimensional object holding a liquid phase internally.

Figure 1:
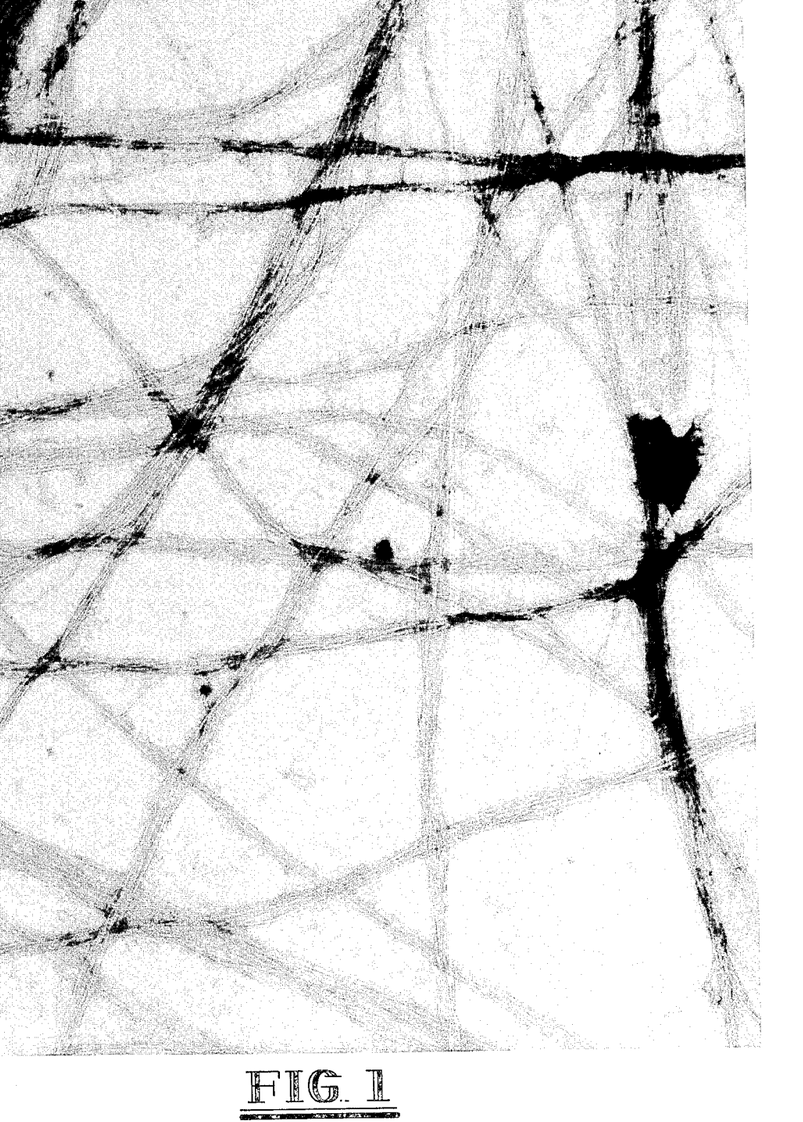
FIG. 1 shows an electron micrograph of dried Acetobacter cellulose produced in the presence of 1% CMC and SH medium minus glucose. The cellulose film consists of only 1–2 layers of cellulosic ribbons and is very thin.

A small piece of this optically clear gelatinous cellulose was washed in distilled water briefly and then gently stretched across the mouth of a 150 ml Erhlenmeyer flask and allowed to air dry. Upon drying, a thin membrane film was produced which exhibited interference colors, suggesting that it was less than 1,000 Angstroms thick. A droplet of water was placed on the surface of a Formvar-coated electron microscope grid and part of the dried pellicle transferred to the grid for examination. FIG. 1 shows an electron micrograph of the cellulosic film. Note the evenly dispersed ribbons. The individual bundles of microfibrils, and the twisting nature of the ribbon normally present with microbial cellulose were absent. This membrane appeared to be only several ribbon-equivalent layers thick, which was confirmed by the presence of the interference colors of the dried film mentioned above.

Figure 2:
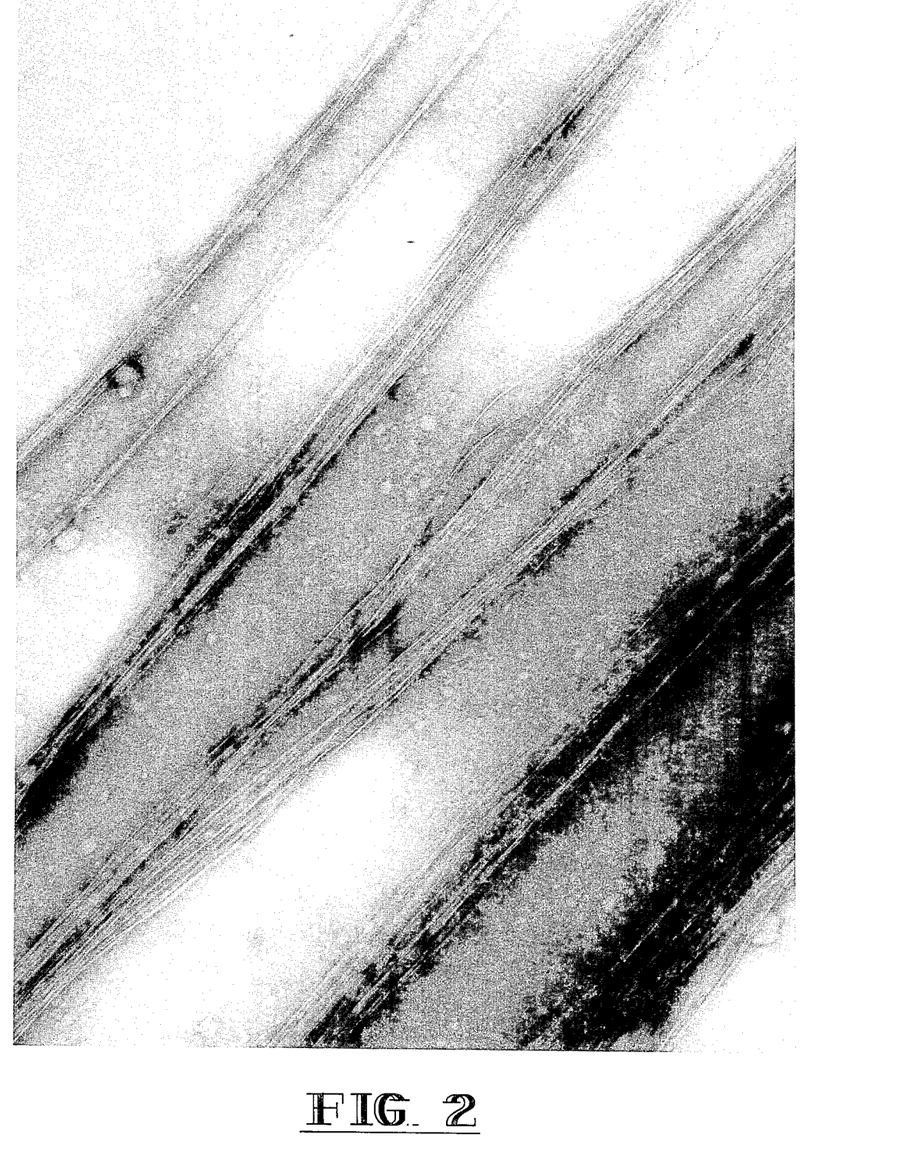
FIG. 2 shows an electron micrograph of Acetobacter cellulose synthesized in the presence of 1% CMC and SH medium minus glucose. The cellulosic ribbons are partially splayed.

The wet cellulosic pellicle was transferred directly to the grid and examined by electron microscopy. The electron micrograph of FIG. 2 revealed a very thin random distribution of cellulose ribbons, similar in general morphology to that produced without CMC, but with the following exceptions: 1) the individual ribbons had a very loose organization of bundles of fibrils; 2) each individual bundle of microfibrils was loosely associated to form the ribbons; 3) long aggregates of ribbons. Thus, the cellulose made in the presence of CMC was not fully integrated into a ribbon. This appearance was similar to what was published earlier but using 0.1% CMC (Haigler et al., (*J. Cell. Biol.* 94:64–69 (1982)).

Figure 3:
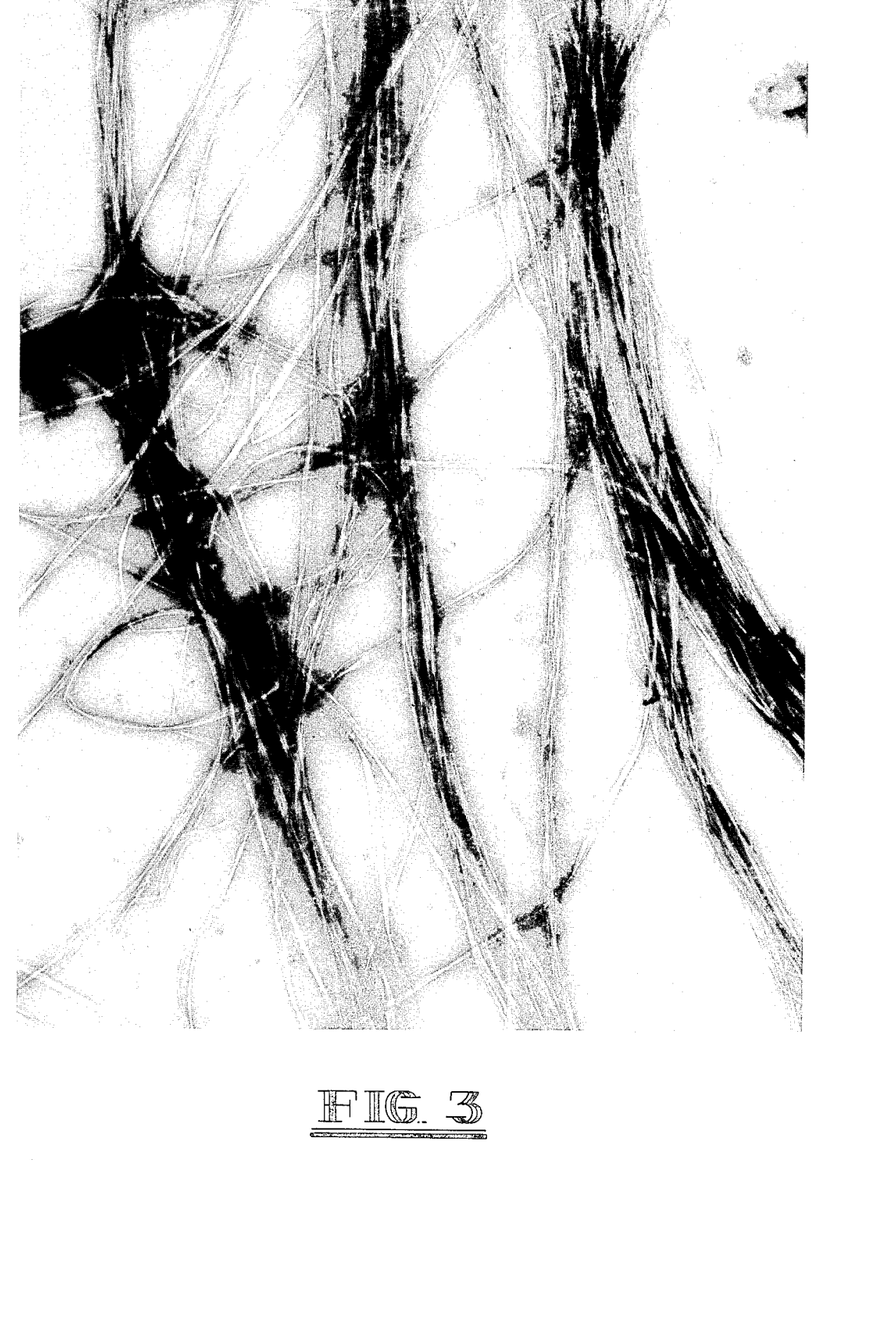
FIG. 3 shows an electron micrograph of cellulose produced by Acetobacter in the presence of SH medium with 2% glucose and 0.1% CMC.

Haigler and Brown published the CMC cultivation procedure using 0.1 wt/vol % to 1.0 wt/vol % CMC. There are major differences in pellicle morphology when using the present high concentrations of CMC. Thus, the present invention advances and is distinguished from the observations in this earlier published paper (Haigler and Brown, *J. Cell Biol.* 94: 64–69, 1982). Nowhere in this earlier work were absorbancy and macroscopic physical properties of the cellulose addressed or predicted. It is significant that with the CMC particularly as used in the present invention, an integral cellulosic membrane was produced with 1% CMC, but 2% and 4% CMC yielded a non-integral cellulose structure. FIG. 3 shows the ultrastructure of cellulose produced under conditions analogous to those described in Haigler and Brown (1982), i.e., in the presence of 0.1% (wt/vol) CMC. Note that most of the cellulose shown in FIG. 3 is organized into bundles of twisting ribbons. Contrast FIG. 3 with FIGS. 1 and 2.

The dried cellulose membrane from 1% CMC-treated cellulose had only one or two, and at most seven or eight layers of ribbons. Since the ribbon has been shown to be approximately 50 Angstroms thick at its flat side, this would support the proof of the thin, dried film which exhibited interference colors. Also, the morphology of the dried cellulose fibrillar ribbons suggests that they were not intimately bound to each other and were probably coated with carboxymethylcellulose.

An optically clear gel was produced by treatment with 1% CMC in SH medium (without added exogenous glucose). This film may be washed with distilled water, air-dried, and rehydrated. Celluloses produced in the absence of CMC also may be dried and rehydrated, but generally not to the same extent as the CMC-grown celluloses.

EXAMPLE 3

Effects of Carboxymethylcellulose-produced Microbial Cellulose Upon the Water-Absorbency of Cotton The control sample was absorbent cotton which was wetted, rubbed briskly between the fingers, dried, rewetted, and the wet and dry weights measured. The experimental sample consisted of absorbent cotton to which CMC-microbial cellulose (i.e. cellulose synthesized in the presence of SH without glucose and containing 2% CMC as described above) was applied and worked into the cotton fibers. The material was dried, rewetted, and wet and dry weights measured. These weights are shown in Table 1.

TABLE 1

| Sample | Weight |
|---|---|
| Control: | dry weight 0.21 g |

TABLE 1-continued

| Sample | Weight |
|---|---|
| Experimental: | wet weight 3.75 g |
|  | dry weight 0.25 g |
|  | wet weight 3.95 g |

The cotton to which CMC-microbial cellulose had been applied had about the same total water absorbency as the control absorbent cotton. One major difference noted was that the CMC-cellulose/cotton mixture absorbed water much more rapidly than the absorbent cotton. A composition of matter for avidly absorbing water which comprises cotton and modified microbial cellulose may thus be prepared. A mixture of this type may have industrial applications, for example, when a more rapid absorption is desired.

EXAMPLE 4

Elastomeric Properties of CMC-produced Microbial Cellulose

Acetobacter cellulose synthesized in the presence of 2% CMC, as described in Example 1 was used for this example. Instead of air-drying however, the cellulose was dried by treatment with hydrophilic solvent.

Acetone has the capability of removing most of the water, but some tightly bound water may not be removed. When a cellulose pellicle was dried with acetone, the physical properties of the cellulose changed considerably. Instead of being slippery, the material took on an elastomeric or rubber-like consistency, e.g., it could be stretched, and would spontaneously return to its original state after stretching.

When the CMC-produced cellulose was dried in absolute ethanol, the dried material had no elasticity or elastomeric properties but was very tough and resilient or leather-like. When water is added to samples dried with either hydrophilic solvent, immediate absorption of the water occurred, and the material returned to its original gel-like state.

The presence, during microbial cellulose synthesis, of a cellulose derivative such as CMC altered the physical properties of cellulose so that novel forms of cellulose were produced. When water was extracted by air-drying or hydrophilic solvents. Novel physical forms of cellulose were manifested.

EXAMPLE 5

Preliminary Absorption, Redrying, and Rewetting Studies With CMC-Modified Microbial Cellulose Acetobacter was grown in Roux bottles of Schramm-Hestrin Hestrin medium minus glucose which contained 2% carboxy-methylcellulose (as described in Example 1). The cultures were allow to grow to completion and pellicle samples were tested when more than one month old. A sample of the clear, highly hydrophilic pellicle was washed with tap water two or three times. Then, a small sample was twisted by hand to form a very tight thread. This procedure removed most of the water. The thread was then heated to dryness in an oven for 15 minutes at 90° C. and then weighed. The dried thread weighed 0.00078g. The dried thread was carefully rehydrated in a beaker of distilled water. Immediately after the thread touched the water, it underwent a violent uncoiling reaction as water was being absorbed. After the uncoiling was complete, the sample was found to weigh 0.09g. The same sample was then gently sonicated and then reweighed. The wet weight now increased to 0.13g. Thus, dividing the wet weight by the dry weight, the cellulose produced in this manner had the ability to absorb more than 177× its weight in water.

The same sample was twisted once again into a fine thread and dried in the manner described above. Its second dry weight was 0.00073 g. Thus, little measurable amount of the microbial cellulose product had been lost, nor had any other major component been lost during the rewetting procedure. This same sample was rewet for a second time, and the wet weight obtained was 0.11 g. This weight gain illustrated the ability of the CMC-cellulose to absorb more than 150X its weight in water following a second rewetting. These observations confirmed that any residual CMC present was tightly bound to the cellulosic structure and did not wash out during the sonication or washing processes.

These observations had interesting implications regarding the interactions of cellulose with bound micellar water, or unbound water. In addition, the tenacity of CMC to the cellulosic product was implicated.

EXAMPLE 6

Determination of Absorptivity of CMC-grown Microbial Cellulose

A Roux bottle containing Schramm-Hestrin medium without exogenously added gucose, and 2% carboxymethylcellulose (as in Example 1) was inoculated with Acetobacter and allowed to grow to completion. The celulosic material tested was produced at 28° C. and was approximately four months old.

The pellicle was transferred to 2% sodium chloride in distilled water and allowed to soak for 3 hrs. The wet weight of the pellicle was 5.73g. This pellicle was squeezed manually by twisting, and then oven-dried. The dry weight of the entire pellicle was 0.007g. (Incidentally, this pellicle weight closely matched weights of pellicles from earlier experiments in which Schramm-Hestrin without exogenously added glucose was also used.)

This entire pellicle then was rewet with 2% sodium chloride, and the wet weight measured. The wet weight was 0.10g. Using 2% sodium chloride in the water, the CMC-produced cellulose absorbed only 14.2X its weight in water. This was quite low in comparison with distilled water, but was expected in the presence of salt solutions.

When the sodium chloride-treated wet pellicle was transferred to a large beaker of distilled water and shaken, the pellicle immediately started swelling. The wet weight of the pellicle now rose to 1.44 g. Thus, in distilled water, this cellulose absorbed more than 205× its weight in water.

The same wet pellicle was then sonicated in distilled water, and the wet weight remeasured. The wet weight of this pellicle increased to 3.48 g, representing the capacity of microbial cellulose to absorb more than 497× its weight of water.

This same pellicle was then oven-dried after a manual squeeze/twist for a second time and weighed. The dry weight was 0.00314 g. About half of the weight had been lost through these manipulations. The pellicle was then rewet again, this time with 2% sodium chloride in distilled water. The wet weight was 0.01 g, representing an ability to absorb only 3.3× the equivalent weight.

This pellicle was transferred once again to distilled water and shaken. The wet weight rose to 0.93 g, representing the ability of the cellulose to absorb 310× its weight in water.

The pellicle was finally sonicated in distilled water, and the weight wet rose dramatically to 1.9 g, representing an ability to absorb more than 633X its weight in water.

The ability of CMC-grown cellulose to absorb distilled water was very great. In this experiment, the dry cellulose weight absorbed up to 633X its weight in water. Although 2% sodium chloride seriously inhibited water absorption, this was reversible when the sodium chloride was removed. Repeated air-drying of the CMC-cellulose did not diminish the absorption capacity, in contrast to cellulose produced only in the presence of Schramm-Hestrin medium alone. Sonication allowed more complete access of water to the cellulose matrices.

EXAMPLE 7

Absorptivity and Yields With CMC-produced cellulose

Acetobacter was grown in Roux bottles (standing cultures) each containing 200 ml of SH medium without exogenously added glucose. The cultures were grown for four days at 28° C. Four different concentrations of CMC were used, in addition to the control which contained no CMC. The pellicles were exhaustively washed with distilled water to remove soluble CMC or other substances and then the wet weight was taken. The pellicles were dried and reweighed. The water absorptivity capacity was measured by dividing the wet weight by the dry weight. The carboxymethylcellulose used in this experiment was from Hercules, and had a degree of substitution of 1.6, and a viscosity of 250,000 cps. Table 2 shows the results of this experiment.

TABLE 2

| CMC Added | Wet Weight | Dry Wet | Wet/Dry |
|---|---|---|---|
| 0% CMC | 17.45 g | 0.025 g | 698 X |
| 0.5% CMC | 23.17 g | 0.027 g | 858 X |
| 1.0% CMC | 40.39 g | 0.033 g | 1223 X |
| 2.0% CMC | 55.13 g | 0.055 g | 1002 X |
| 4.0% CMC | 80.0 g | 0.753 g | 106 X |

The dried cellulosic films produced from stretched 1% CMC-grown material showed interference colors (indicating that the dried pellicle films had a thickness of 1000 Angstroms or less). All dry pellicles were very fragile, except for the one produced in the presence of 4% CMC which was extremely strong and quite optically clear.

The birefringence of the dried celluloses was measured using polarization optics on a stereo microscope, and the degree of birefringence estimated. Table 3 gives qualitative results from the birefringence studies.

TABLE 3

| Birefringence of CMC-cellulose | |
|---|---|
| 0% CMC | ++++ birefringence |
| 0.5% CMC | +++ birefringence |
| 1% CMC | ++ birefringence |
| 2% CMC | ++++ birefringence |
| 4% CMC | ++ birefringence |

The results of birefringence studies were somewhat variable, but basically all of the dried celluloses exhibited a considerable degree of birefringence, thus implying that the cellulose was quite highly ordered. Depending upon the concentration of CMC used, the absorptivity varied, with a maximum of absorptivity being reached when 1% CMC was used. In this case, the cellulose absorbed over 1223X its weight of water. This process was also reversible. A second tentative conclusion from these observations related to the molecular order of dried cellulose made in the presence of CMC. This cellulose was highly birefringent and exhibited considerable molecular order.

EXAMPLE 8

Effect of Glucose and CMC Concentration on The Mass and Absorptive Characteristics of *Acetobacter xylinum* Pellicles Produced in Examples 1–7

There was a generally inverse relationship between glucose concentration in the medium and initial absorptivity. Pellicles formed on SH with 0% glucose exogenously added and no CMC had an approximately 700× absorptive ratio (absorptive ratio = wet weight/dry weight) compared to 40× for pellicles derived from SH with 2% glucose (no CMC). The negative effect of the glucose concentration on initial absorptivity of cellulose was statistically significant between 0% and 0.1% glucose concentrations, the difference in absorptivity being a factor greated than 7 fold. In contrast, the difference in cellulose absorptivity between 0.1% and 2% glucose concentration was less than 2.5 fold.

At a glucose concentration greater than 0.1%, CMC concentration had little effect on initial absorptivity. At a glucose concentration less than 0.1% (i.e., 0% glucose exogenously added), increasing the CMC concentration increased the absorptivity up to a CMC concentration of 1%, and then decreased thereafter.

Repeated wetting and drying of pellicles not grown in the presence of CMC showed a sharp and significant drop in absorptivity. The observation was consistent for pellicles grown at all glucose concentrations, but appeared to be more pronounced at the lower glucose concentrations.

Repeated wetting and drying and weighing of pellicles grown in the presence of CMC and at low glucose concentrations (i.e., 0–0.1% glucose concentration) showed an increasing absorptivity through two wet/dry cycles. The initial absorptive ratio of 0.1% glucose/0.5–1% CMC produced pellicles was approximately 58×. The absorptive ratio rose to approximately 180× after two wet/dry cycles.

For pellicles grown in a medium containing more than 0.1% glucose, absorptivity was observed to rise slightly upon the first rewetting and fall to levels at or below the initial absorptivity on the third rewetting. A rise in absorptivity upon rewetting was found with pellicles grown in 0.5–0.75% glucose concentration, as was a fall in absorptivity upon rewetting. For pellicles formed in glucose concentrations equal to or greater than 1%, absorptivity rose upon rewetting only when the CMC concentrations was equal to or greater than 1%. At less than 1% CMC concentration, absorptivity either did not change or declined very slightly in wetting/drying cycles. Upon the second rewetting, absorptivity declined in nearly all samples in an inverse relation to the CMC concentration in which they were produced. Pellicles from in high glucose and high CMC concentrations seemed to maintain their absorptivity upon repeated wetting/drying, whereas with pellicles grown in intermediate levels of glucose, the absorptivity first rose and then fell below the initial absorptivity value.

An interrelationship between the glucose medium, CMC concentration, and the initial and subsequent absorptive capacity of *A. xylinum* pellicles was apparent. Initial absorptivity was highest at the lowest glucose concentration, but repeated absorptive capacity was best maintained at high glucose concentrations Increasing CMC concentration tended to sometimes retard initial absorptivity, but resulted in a maintained or enhanced absorbence after repeated wetting and drying.

Initial wet weight yields were not always related to the glucose concentration, as most glucose controls (without CMC) weighed about the same (about 50 g); however, initial wet weight appears to be inversely related to CMC concentration. At CMC concentrations equal to or greater than 2%, initial wet weights may be less than ⅜ that of glucose controls. This effect was slightly more pronounced at higher glucose concentrations.

Wet weights after repeated wetting cycles did not appear to be related to the glucose concentration; however, they were affected by the CMC concentration. Increasing CMC concentrations reduced the loss in wet weight observed after repeated rewetting. Typically, the samples with the highest CMC concentrations had the lowest initial wet weight, but had the highest wet weight after two rewettings. Nevertheless, even at the highest CMC concentration there was significant wet weight loss after two rewettings. The data suggested that the CMC was leaching out of the pellicle upon repeated rewetting, and pellicles which contained the most CMC most effectively retained their wet weight.

Initial dry weight yields were directly related to the glucose concentration in the nutrient medium. These weight yields ranged from as low as 0.025 g in 0% exogenously added glucose medium-derived pellicles, to as high as 1.21 g for those from 2% glucose medium, a 48 fold difference in yield. However, the carbon utilization efficiency with respect to glucose was inversely related to the medium glucose concentration. Carbon utilization efficiencies with respect to glucose ranged from theoretically almost 100% for 0% exogenously added glucose derived pellicles to 30% for 2% glucose derived pellicles. This effect was evident in the tapering off of the increase in initial dry weight yields as the glucose concentration increased. There appeared to be no discernable relationship between CMC concentration in the medium and initial dry weight yield. At low glucose concentrations (equal to or less than 0.5%), and at high glucose concentrations (2%), increasing CMC concentration increased initial dry weight yields, but at intermediate glucose concentrations (0.75–1%), initial dry weight yields decreased with increasing CMC concentration.

Pellicle dry weight yields decreased by 30–60% after vigorous washing in warm water, but dry weight yields did not decrease significantly after subsequent rewetting. The effect of warm water washing and subsequent rewetting on pellicle dry weight yields appeared to be independent of the glucose concentration or CMC concentration; however, treatment of the pellicles with 4% sodium hydroxide reduced the dry weight yield of pellicles containing CMC by 11%, while reducing dry weight yield in CMC-free pellicles by only 4%.

Initial and subsequent wet weights were not invariably related to the glucose concentration. CMC concentration, however, had a significant effect on pellicle wet weight. CMC reduced initial wet weight values, but improved wet weight retention after repeated drying and wetting. Optimizing CMC concentration and incorporation may improve pellicle "rewettability". Initial pellicle dry weight yields were often directly related to the glucose concentration, but not to the CMC concentration. Carbon utilization efficiency with respect to glucose concentration was extremely high at lower glucose concentration, but decreased significantly with increasing glucose concentrations. This latter effect suggested that cellulose synthesis may be repressed by high glucose concentrations. Pellicle dry weight yields were significantly reduced by warm water washing, but appeared to be relatively unaffected by rewetting. These observations were independent of initial glucose concentrations or CMC concentrations. Treatment of pellicles with 4% sodium hydroxide reduced the dry weight yields of pellicles grown in the medium containing CMC slightly more than it did in the dry weight yields of pellicles grown in CMC-free medium.

Higher initial absorptivity observed in pellicles derived from low glucose concentration medium may be attributed to their lower initial dry weight rather than to a difference in relative wet weight yield values.

EXAMPLE 9

Effects of Nutrient Medium, Cellulose Derivative Type and Concentration upon the Amount and Characteristics of Microbial Cellulose Utilizing the conditions and methods generally described in Examples 1–8, the effects of other nutrient media and cellulose derivatives upon microbial cellulose production and absorbency were studied.

Nutrient media studied included: normal Schramm-Hestrin medium having 2% glucose (SH or SH (normal)); Schramm-Hestrin medium without exogenously added glucose (SH-gluc or 0% gluc); Schramm-Hestrin medium with various glucose concentrations instead of the normal 2% (SH 0.1% gluc, 0.5% gluc, 0.75% gluc or 1.0% gluc); Schramm-Hestrin medium at double strength (2 SH); Schramm-Hestrin medium at half strength (½ SH ; Schramm-Hestrin medium with additional peptone protein (SH +2% protein); Schramm-Hestrin medium with 1% glucose and additional peptone protein (SH +1% gluc +2% protein); and corn steep liquor.

Additional cellulose derivatives studied included: methyl cellulose (MC); hydroxyethylcellulose (HEC); hydroxypropylcellulose (HPC); and hydroxypropylmethylcellulose (HPMC).

Table 4 shows effects of nutrient medium on Acetobacter pellicle weights before and after washing and repeated dryings and rewettings.

TABLE 4

EFFECT OF MEDIUM ON ACETOBACTER PELLICLE WEIGHTS AND ABSORBENCY

| Nutrient Medium | Original Wet Wt. | Wet Wt. #1[a] | Dry Wt. #1[a] | Wet Wt. #2[a] | Dry Wt. #2[a] | Wet Wt. #3 | Dry Wt. Final | Wet Wt. #1 Dry Wt. #1 | Rewet Wt. #1 Redry wt. #1 | Rewet wt. #2 Final Dry Wt. |
|---|---|---|---|---|---|---|---|---|---|---|
| Corn Steep Liquor | 37.9 | 39.14[b] | 0.44 | 1.85 | 0.39 | 2.0 | 0.39 | 61[b] | 5 | 5 |
| 2 SH | | 55.34[b] | 0.71 | 3.13 | 0.63 | 2.77 | 0.62 | 86[b] | 5 | 4.5 |
| ½ SH | 33.76[c] | 30.62[d] | 0.42[e] | 3.68 | 0.31 | 2.01 | 0.31 | 51 | 12 | 6.5 |
| SH + 2% Protein | 41.15 | 46.19 | 1.13 | 11.39 | 0.63 | 3.53 | 0.60 | 41 | 18 | 6 |
| SH + 1% Gluc + 2% Protein | 26.13 | 17.16 | 0.40 | 2.42 | 0.26 | 1.02 | 0.25 | 43 | 9 | 4 |

[a] = Mean sample weight in grams
[b] = Derived from 2 samples
[c] = Derived from 6 samples
[d] = Derived from 5 samples
[e] = Derived from 8 samples The yields and absorbency characteristics were measured for microbial cellulose from Acetobacter-produced cellulosic pellicles formed in normal Schramm-Hestrin medium (SH), Schramm-Hestrin medium devoid of exogenously added glucose (SH-gluc), SH-gluc with 2% CMC and SH-gluc with 4% CMC. Table 5 shows weight and absorbency data obtained.

TABLE 5

EFFECT OF NUTRIENT AND CMC

| Nutrient Medium and Additions | Original[a] Wet Wt. #1 | Washed[a] Wet Wt. #2 | Dry Wt. #1[a] | Absorptive Ratio #1 | Rewet Wt. #1 | Redry Wt. #1 | Absorptive Ratio #2 | Rewet Wt. #2[a] | Redry Wt. #2[a] | Absorptive Ratio #3 |
|---|---|---|---|---|---|---|---|---|---|---|
| SH-Gluc | 20.28 | 19.07 | 0.14 | 136.2 | 4.82 | 0.04 | 120.5 | 3.37 | 0.02 | 169.0 |
| | 24.76 | 20.62 | 0.14 | 147.3 | 6.00 | 0.03 | 200.0 | 2.36 | 0.012 | 191.9 |
| | 22.42 | 17.20 | 0.13 | 132.3 | 10.08 | 0.05 | 201.6 | 6.74 | 0.02 | 337.0 |
| | 23.06 | 21.13 | 0.16 | 132.1 | 9.62 | 0.07 | 137.4 | 4.76 | 0.02 | 238.8 |
| Average | 22.63 | 19.51 | 0.14 | 139.3[b] | 7.63 | 0.05 | 160.6[b] | 4.31 | 0.018 | 238.5[b] |
| SH (normal) | 71.75 | 86.26 | 2.35 | 36.7 | 18.52 | 1.29 | 14.4 | 5.43 | 1.22 | 4.5 |
| | 71.60 | 85.48 | 2.42 | 35.3 | 19.73 | 1.35 | 14.6 | 5.59 | 1.24 | 4.5 |
| | 70.29 | 87.91 | 2.36 | 37.3 | 19.56 | 1.30 | 15.1 | 5.16 | 1.25 | 4.1 |
| | 72.19 | 85.10 | 2.32 | 36.7 | 17.91 | 1.28 | 14.0 | 4.78 | 1.26 | 3.8 |
| Average | 71.46 | 86.19 | 2.36 | 36.5[b] | 18.93 | 1.31 | 14.5[b] | 5.24 | 1.24 | 4.2[b] |
| 2% CMC + SH-Gluc | 81.10 | 32.80 | 0.87 | 37.7 | 28.57 | 0.48 | 59.5 | 26.85 | 0.22 | 122.0 |
| | 92.01 | 47.30 | 0.85 | 55.7 | 41.79 | 0.64 | 65.3 | 25.55 | 0.22 | 116.0 |
| | 70.61 | 30.83 | 0.44 | 70.1 | 18.50 | 0.16 | 115.6 | 17.17 | 0.04 | 429.0 |
| Average | 81.24 | 36.98 | 0.72 | 51.4[b] | 29.62 | 0.43 | 69.4[b] | 23.19 | 0.16 | 145.0[b] |
| 4% CMC + SH-Gluc | 109.83 | 103.83 | 4.38 | 23.7 | 84.31 | 3.43 | 24.6 | 41.77 | 2.30 | 18.2 |
| | 120.56 | 114.90 | 5.07 | 22.7 | 69.36 | 3.90 | 17.8 | 37.24 | 2.75 | 13.5 |
| | 118.70 | 111.47 | 5.28 | 21.1 | 64.67 | 3.89 | 16.6 | 40.44 | 2.73 | 14.8 |

TABLE 5-continued

| | EFFECT OF NUTRIENT AND CMC | | | | | | | | | |
|---|---|---|---|---|---|---|---|---|---|---|
| Nutrient Medium and Additions | Original[a] Wet Wt. #1 | Washed[a] Wet Wt. #2 | Dry Wt. #1[a] | Absorptive Ratio #1 | Rewet Wt. #1 | Redry Wt. #1 | Absorptive Ratio #2 | Rewet Wt. #2[a] | Redry Wt. #2[a] | Absorptive Ratio #3 |
| Average | 116.36 | 110.07 | 4.91 | 22.4[b] | 72.78 | 3.79 | 19.5[b] | 39.82 | 2.59 | 15.35[b] |

[a] = All weights in grams
[b] = The mean absorptive ratio is calculated by dividing the average wet weight by the corresponding average dry weight.

As seen in Table 5, the CMC appeared to enhance both the yield of cellulose and the amount of cellulose remaining after repeated washings.

In a further test, the effects upon microbial cellulose of Acetobacter growth in several CMC concentrations in Schramm-Hestrin medium with various amounts of glucose were determined. Table 6 shows the data resulting from such manipulations.

after extensive washing, and to increase the absorbency of the product microbial cellulose.

The effects of other cellulose derivatives upon microbial cellulose production and characteristics thereof were studied. The additional cellulose derivatives studied were: methyl cellulose (MC); hydroxyethylcellulose (HEC); hydroxypropylcellulose (HPC); and hydroxypropylmethylcellulose (HPMC). Table 7 shows the

TABLE 6

EFFECTS OF GLUCOSE AND CMC CONCENTRATIONS ON ACETOBACTER PELLICLE WEIGHTS AND ABSORPTIVE RATIOS

| Nutrient Medium and Additions | Avg.[a] Original Wet Wt. #1 | Avg.[a] Wet Wt. #2 | Avg.[a] Dry Wt. #1 | Avg.[b] Wet Wt. #1 Dry Wt. #1 | Avg. Wet Wt. #2 | Avg.[1] Dry Wt. #2 | Avg.[b] Wet Wt. #2 Dry Wt. #2 | Avg.[a] Wet Wt. #3 | Avg.[a] Final Dry Wt. | Avg.[b] Wet Wt. #3 Final Dry Wt. |
|---|---|---|---|---|---|---|---|---|---|---|
| SH-Gluc | | 17.25 | 0.025 | 690 | | | | | | |
| SH-Gluc + 0.5% CMC | | 23.17 | 0.027 | 858 | | | | | | |
| SH-Gluc + 1.0% CMC | | 40.39 | 0.033 | 1,234 | | | | | | |
| SH-Gluc + 2.0% CMC | | 55.13 | 0.055 | 1,002 | | | | | | |
| SH-Gluc + 4.0% CMC | | 80.0 | 0.753 | 106 | | | | | | |
| SH-Gluc | | 10.02 | 0.0533 | 188 | 0.77[c] | 0.012[c] | 64[d] | 0.06112[c] | 0.01198[c] | 510[d] |
| SH-Gluc + 0.5% CMC | | 11.40 | 0.0885 | 129 | 5.90[c] | 0.016[c] | 369[d] | 1.39[c] | 0.0136[c] | 102[d] |
| SH-Gluc + 4.0% CMC | | 20.57 | 0.753 | 27 | 10.21[c] | 0.349[c] | 29[d] | 12.27[c] | 0.139[c] | 88[d] |
| SH + 0.1% Gluc | | 15.04 | 0.17 | 88 | 1.90 | 0.054 | 35 | 0.23[c] | 0.0336[c] | 68[d] |
| SH + 0.1% Gluc + 0.5% CMC | | 27.15 | 0.47 | 58 | 15.15 | 0.215 | 70 | 9.94[c] | 0.0560[c] | 178[d] |
| SH + 0.1% Gluc + 1.0% CMC | | 26.52 | 0.49 | 54 | 21.18 | 0.311 | 68 | 12.34[c] | 0.0648[c] | 190[d] |
| SH + 0.1% Gluc + 2.0% CMC | | 29.28 | 0.71 | 41 | 23.51 | 0.420 | 56 | 13.20[c] | 0.410[c] | 32[d] |
| SH + 0.5% Gluc | 49.0 | 40.44 | 0.76 | 54 | 14.0 | 0.39 | 35 | 2.77 | 0.30–0.41 | 7–9 |
| SH + 0.5% Gluc + 0.5% CMC | 67.29 | 40.99 | 0.88 | 47 | 25.27 | 0.44 | 58 | 8.07 | " | 20–27 |
| SH + 0.5% Gluc + 1.0% CMC | 45.63 | 34.24 | 0.87 | 39 | 27.44 | 0.42 | 66 | 10.90 | " | 27–36 |
| SH + 0.5% Gluc + 2.0% CMC | 53.01 | 35.65 | 1.12 | 32 | 30.93 | 0.44 | 70 | 16.23 | " | 40–54 |
| SH + 0.75% Gluc | 50.74 | 54.75 | 1.16 | 47 | 10.55 | 0.61 | 17 | 2.90 | 0.60 | 5 |
| SH + 0.75% Gluc + 0.5% CMC | 45.79 | 47.62 | 1.19 | 40 | 25.50 | 0.65 | 39 | 9.67 | 0.60 | 16 |
| SH + 0.75% Gluc + 1.0% CMC | 46.99 | 40.21 | 1.13 | 36 | 26.55 | 0.68 | 39 | 11.57 | 0.61 | 19 |
| SH + 0.75% Gluc + 2.0% CMC | 32.78 | 26.11 | 1.01 | 26 | 23.64 | 0.56 | 42 | 13.07 | 0.51 | 26 |
| SH + 0.75% Gluc + 4.0% CMC | 33.28 | 27.20 | 0.98 | 28 | 21.81 | 0.54 | 40 | 14.67 | 0.49 | 30 |
| SH + 1% Gluc + 0.5% CMC | 53.74 | 54.67 | 1.55 | 35 | 27.41 | 0.91 | 30 | 11.72 | 0.80 | 15 |
| SH + 1% Gluc + 1.0% CMC | 47.04 | 44.38 | 1.50 | 30 | 29.43 | 0.89 | 33 | 13.21 | 0.74 | 18 |
| SH + 1% Gluc + 2.0% CMC | 38.40 | 30.70 | 1.21 | 25 | 25.01 | 0.74 | 34 | 13.18 | 0.68 | 19 |
| SH + 1% Gluc + 4.0% CMC | 29.25 | 27.41 | 1.24 | 22 | 23.38 | 0.75 | 31 | 17.85 | 0.67 | 27 |
| SH | 47.61 | 48.65 | 1.21 | 40 | 12.09 | 0.63 | 19 | 5.34 | 0.59 | 9 |
| SH + 0.5 CMC | 51.28 | 49.75 | 1.52 | 33 | 31.21 | 0.87 | 36 | 14.69 | 0.77 | 19 |
| SH + 1.0 CMC | 36.82 | 39.75 | 1.47 | 27 | 32.28 | 0.83 | 39 | 14.87 | 0.71 | 21 |
| 2% CMC | | 35.80 | 1.36 | 26 | 30.25 | 0.95 | 32 | 12.16 | 0.92 | 13 |

[a] = All weights in grams
[b] = Mean absorptive ratio is calculated from the average wet weight divided by the corresponding dry weight
[c] = Weight based on partial pellicle recovery
[d] = Calculation based on average weight of pellicle recovered The data in Table 6 indicated that the CMC tended to increase both the weight of cellulose produced, even effects of these derivatives upon Acetobacter cellulose produced in Schramm-Hestrin medium (SH) without exogenously added glucose.

TABLE 7

WEIGHTS AND ABSORPTIVE RATIOS OF ACETOBACTER CELLULOSE
PRODUCED IN THE PRESENCE OF CELLULOSE DERIVATIVES

| Sample | Original[a] Wet Wt. #1 | Washed[a] Wet Wt. #2 | Dry Wt. #1[a] | Absorptive Ratio #1 | Rewet Wt. #1[a] | Redry Wt. #1[a] | Absorptive Ratio #2 | Rewet Wt. #2[a] | Redry Wt. #2[a] | Absorptive Ratio #3 |
|---|---|---|---|---|---|---|---|---|---|---|
| 2% MC | 84.57 | 30.19 | 0.44 | 68.6 | 15.26 | 0.13 | 117.4 | 14.37 | 0.04 | 359 |
|  | 99.68 | 29.71 | 0.56 | 53.05 | 21.86 | 0.26 | 84.1 | 16.97 | 0.09 | 189 |
|  | 58.49 | 19.26 | 0.32 | 60.19 | 17.10 | 0.12 | 142.5 | 12.11 | 0.03 | 404 |
| Average | 80.91 | 26.39 | 0.44 | 60.0[b] | 18.07 | 0.17 | 106.3[b] | 14.48 | 0.05 | 272[b] |
| 2% HEC | 67.27 | 18.61 | 0.22 | 84.6 | 17.60 | 0.12 | 146.7 | 17.78 | 0.05 | 356 |
|  | 58.30 | 20.73 | 0.31 | 66.9 | 17.50 | 0.15 | 116.7 | 18.98 | 0.09 | 211 |
|  | 84.67 | 28.82 | 0.39 | 73.9 | 16.54 | 0.25 | 66.2 | 23.85 | 0.16 | 149 |
| Average | 70.08 | 22.72 | 0.31 | 74.10[b] | 17.21 | 0.17 | 99.3[b] | 20.2 | 0.10 | 202[b] |
| 2% HPC | 68.68 | 42.48 | 0.75 | 56.6 | 26.19 | 0.42 | 62.4 | 18.72 | 0.18 | 104 |
|  | 54.54 | 31.03 | 0.72 | 43.1 | 26.38 | 0.46 | 57.4 | 19.57 | 0.26 | 75.3 |
|  | 64.48 | 33.12 | 0.88 | 37.6 | 27.76 | 0.60 | 46.3 | 19.43 | 0.25 | 77.7 |
| Average | 62.57 | 35.54 | 0.78 | 45.4[b] | 26.78 | 0.49 | 54.3[b] | 19.24 | 0.23 | 83.7[b] |
| 2% HPMC | 91.88 | 39.92 | 0.86 | 46.0 | 31.93 | 0.42 | 76.0 | 20.44 | 0.19 | 107.6 |
|  | 77.56 | 11.07 | 0.20 | 55.4 | 9.50 | 0.03 | 316.7 | 4.49 | 0.0045 | 993.4 |
|  | 111.26 | 44.89 | 1.04 | 43.2 | 32.17 | 0.59 | 54.53 | 22.12 | 0.28 | 79.0 |
| Average | 93.6 | 31.83 | 0.70 | 45.5[b] | 24.53 | 0.35 | 70.1[b] | 15.68 | 0.16 | 99.0[b] |

[a] = All weights in grams
[b] = Average absorptive ratio was calculated by dividing the average wet weight by the corresponding averaged dry weight As may be seen in the data of Table 7, the cellulose derivatives tended to increase the weight of cellulose produced and to increase the absorbency of product cellulose, particularly after repeated rewettings and dryings.

Changes may be made in the cellulose-producing microorganisms, mutrient media, steps and procedures described herein without departing from the concept and scope of the invention as defined in the following claims.

What is claimed is:

1. A process for producing modified cellulose, the process comprising:
   inoculating a quantity of nutrient medium comprising between about 1.0% and about 5.0% polysaccharide derivative with a cellulose-producing microorganism;
   aerobically incubating the inoculated medium to produce modified cellulose therein; and
   collecting the cellulose.

2. A process for producing a water absorbent, the process comprising:
   inoculating a quantity of nutrient medium comprising between about 0.1% and about 5.0% polysaccharide derivative with a cellulose-producing microorganism;
   aerobically incubating the inoculated medium to produce modified cellulose therein;
   collecting the cellulose; and
   drying the cellulose.

3. The process of claim 1 or 2 wherein the cellulose-producing microorganism is an Acetobacter.

4. The process of claim 1 or 2 wherein the polysaccharide derivative is a cellulose derivative.

5. The process of claim 4 wherein the cellulose derivative is at least one of carboxymethylcellulose, methylcellulose, hydroxyethylcellulose, hydroxypropylcellulose and hydroxypropylmethylcellulose.

6. The process of claim 4 wherein the cellulose derivative is carboxymethylcellulose.

7. The process of claim 4 wherein the cellulose derivative is at a concentration between about 2 wt/vol % and about 4 wt/vol %.

8. The process of claim 6 wherein the carboxymethylcellulose is at a concentration between about 2 wt/vol % and about 4 wt/vol %.

9. The process of claim 6 wherein the carboxymethylcellulose has a degree of substitution between about 0.4 and about 1.2 carboxymethyl groups per monosaccharide unit.

10. The process of claim 2 wherein the cellulose is dried with a non-aqueous hydrophilic solvent.

11. The process of claim 10 wherein the non-aqueous hydrophilic solvent is an alkyl alcohol or ketone having less than about six carbon atoms.

12. The process of claim 10 wherein the drying step results in a cellulose with a resilient structure.

13. The process of claim 1 or 2 wherein the modified cellulose is optically transparent.

14. The process of claim 2 wherein the modified cellulose is characterized further as being highly absorbent.

15. The process of claim 2 wherein the modified cellulose is defined further as being highly absorbent and retaining high absorptivity through at least several cycles of wetting and drying.

16. The process of claim 1 or 2 wherein the polysaccharide derivative has substituents selected from the group consisting of alkyl, alkylhydroxy, alkylcarboxy, sulfate and phosphate.

17. The process of claim 1 or 2 wherein the polysaccharide derivative is hydrophilic.

18. A composition of matter comprising cellulose formed by a cellulose-producing microorganism in a nutrient medium comprising between about 0.1% and about 5.0% polysaccharide derivative said cellulose being dried.

19. The composition of matter of claim 18 defined further as being dried by air drying or washing with a non-aqueous hydrophilic solvent.

20. The composition of matter of claim 18 or 19 wherein the cellulose-producing microorganism is an acetobacter.

21. The composition of matter of claim 18 or 19 wherein the polysaccharide derivative is a cellulose derivative.

22. The composition of matter of claim 21 wherein the cellulose derivative is at least one of carboxymethylcellulose methylcellulose, hydroxyethylcellulose, hydroxypropylcellulose or hydroxypropylmethylcellulose.

23. The composition of matter of claim 21 wherein the cellulose derivative is at a concentration between about 1 wt/vol % and about 4 wt/vol %.

24. The composition of matter of claim 21 wherein the cellulose derivative is carboxymethylcellulose.

25. The composition of matter of claim 24 wherein the carboxymethylcellulose is at a concentration between about 1 wt/vol % and about 4 wt/vol %.

26. The composition of matter of claim 24 wherein the carboxymethylcellulose has a degree of substitution between about 0.4 and about 1.2 carboxymethyl groups per monosaccharide unit.

27. The composition of matter of claim 19 wherein the non-aqueous hydrophilic solvent is an alkyl alcohol or ketone having less than about six carbon atoms.

28. The composition of matter of claim 19 defined further as having a resilient structure.

29. The composition of matter of claim 18 or 19 wherein the modified cellulose is optically clear.

30. The composition of matter of claim 18 or 19 wherein the modified cellulose is characterized further as being highly absorbent.

31. The composition of matter of claim 18 or 19 wherein the modified cellulose is defined further as being highly absorbent and retaining high absorptivity through at least several cycles of wetting and drying.

32. The composition of matter of claim 18 or 19 wherein the polysaccharide derivative has substituents selected from the group consisting of alkyl, alkylhydroxy, alkylcarboxy, sulfate and phosphate.

33. The composition of matter of claim 18 or 19 wherein the polysaccharide derivative is hydrophilic.

34. A composition of matter avidly absorbing water and comprising cotton and modified cellulose produced by a cellulose-producing microorganism in the presence of a nutrient medium comprising between about 0.1% and about 5% polysaccharide derivative.

35. The composition of matter of claim 34 wherein the polysaccharide derivative is methylcellulose, hydroxyethylcellulose, hydroxypropylecellulose or hydroxypropylmethylcellulose.

36. A process for preparing an absorbent, the process comprising the steps of:
cultivating cellulose-producing Acetobacter in a nutrient medium comprising at least 0.1% hydrophilic polysaccharide derivative;
collecting cellulose produced by the Acetobacter; and
drying said collected cellulose to produce an absorbent.

37. A process for absorbing water, the process comprising the steps of:
cultivating cellulose-producing Acetobacter in a nutrient medium comprising at least 0.1% hydrophilic polysaccharide derivative;
collecting cellulose produced by the Acetobacter;
drying said collected cellulose to produce an absorbent material; and
contacting said absorbing material with water.

38. A process for repeatedly absorbing water with the same absorbent, the process comprising the steps of:
cultivating cellulose-producing Acetobacter in a nutrient medium comprising at least 0.1% hydrophilic polysaccharide derivative;
collecting cellulose produced by the Acetobacter;
drying said collected cellulose to produce an absorbent material;
contacting said absorbing material with water to produce a wetted material;
redrying the wetted material; and
recontacting the redryed material with water.

39. A process for producing a membrane comprising cellulose, the process comprising the steps of:
cultivating cellulose-producing Acetobacter in a nutrient medium comprising at least 0.1% hydrophilic polysaccharide derivative to produce a pellicle; stretching said pellicle to produce a membrane; and drying said membrane.

40. The process of claim 39 wherein the membrane has a thickness of less than 1000 Angstroms.

41. The process of claim 36, 37, 38, 39 or 40 wherein the hydrophilic polysaccharide derivative is carboxymethylcellulose.

42. The process of claim 41 wherein the carboxymethylcellulose is at a concentration of between about 2 wt/vol % and about 5 wt/vol %.

43. A process for producing a cotton-based absorbent, the process comprising:
cultivating cellulose-producing Acetobacter in a nutrient medium comprising at least about 2.0% hydrophilic polysaccharide derivative;
collecting cellulose produced by the Acetobacter; and
applying said collected cellulose to cotton.

44. A process for preparing a cellulosic item having an elastomeric, rubber-like consistency, the process comprising the steps of:
cultivating cellulose-producing Acetobacter in a nutrient medium comprising at least 0.1% hydrophilic polysaccharide derivative;
collecting cellulose produced by the Acetobacter; and
drying said collected cellulose with a hydrophilic organic solvent.

45. The process of claim 44 wherein the hydrophilic organic solvent is acetone.

46. A process for preparing a cellulosic item having a non-elastic, tough and resilient consistency, the process comprising the steps of:
cultivating cellulose-producing Acetobacter in a nutrient medium comprising at least 0.1% hydrophilic polysaccharide derivative;
collecting cellulose produced by the Acetobacter; and
drying said collected cellulose with an anhydrous hydrophilic organic solvent.

47. The process of claim 46 wherein the anhydrous hydrophilic organic solvent is absolute ethanol.

48. A process for preparing an optically clear cellulosic gel, the process comprising the steps of:
cultivating cellulose-producing Acetobacter in a nutrient medium without exogenous glucose and comprising from about 2 wt/vol % to about 4 wt/vol % hydrophilic polysaccharide derivative; and
collecting cellulose gel produced by the Acetobacter.

49. The process of claim 48 wherein the hydrophilic polysaccharide is caraboxymethylcellulose.

* * * * *

UNITED STATES PATENT AND TRADEMARK OFFICE
CERTIFICATE OF CORRECTION

PATENT NO. : 4,942,128

DATED : July 17, 1990

INVENTOR(S) : R. Malcolm Brown, Jr., Austin, Texas

It is certified that error appears in the above—identified patent and that said Letters Patent is hereby corrected as shown below:

In claim 20, column 16, line 60 delete the term "acetobacter" and insert the term --Acetobacter--.

In claim 42, column 18, line 21 delete the numeral "2" and insert the numeral --1--.

Signed and Sealed this

Twenty-eighth Day of April, 1992

Attest:

HARRY F. MANBECK, JR.

Attesting Officer     Commissioner of Patents and Trademarks